(12) United States Patent
Ruskewicz

(10) Patent No.: US 6,443,151 B1
(45) Date of Patent: Sep. 3, 2002

(54) FLUID VELOCITY-SENSITIVE TRIGGER MECHANISM

(75) Inventor: Stephen John Ruskewicz, Kensington, CA (US)

(73) Assignee: Aradigm Corporation, Hayward, CA (US)

( * ) Notice: Subject to any disclaimer, the term of this patent is extended or adjusted under 35 U.S.C. 154(b) by 0 days.

(21) Appl. No.: 09/520,923

(22) Filed: Mar. 8, 2000

(51) Int. Cl.[7] .............................................. A61M 15/00
(52) U.S. Cl. ............................ 128/203.15; 128/203.12; 128/200.24
(58) Field of Search ................. 128/200.24, 203.12, 128/203.15; 604/58; 251/12, 42, 298, 301; 73/249; 222/2, 630, 544

(56) References Cited

U.S. PATENT DOCUMENTS

| | | | | |
|---|---|---|---|---|
| 5,217,004 A | * | 6/1993 | Blasnik et al. | 128/200.23 |
| 5,347,998 A | * | 9/1994 | Hodson et al. | 128/200.23 |
| 5,823,179 A | | 10/1998 | Grychowski et al. | |
| 5,848,587 A | | 12/1998 | King | |
| 5,954,047 A | | 9/1999 | Armer et al. | |

* cited by examiner

Primary Examiner—Glenn K. Dawson
(74) Attorney, Agent, or Firm—Paula A. Borden; Bozicevic, Field & Francis, LLP

(57) ABSTRACT

The invention provides a triggering mechanism for actuating a trigger signal in response to a pre-determined rate of fluid flow through the mechanism. Triggering mechanism generally includes a sliding piston within an air channel, held in place by a resistance structure. Further provided are aerosol delivery devices having triggering mechanism.

17 Claims, 12 Drawing Sheets

FLUID VELOCITY-SENSITIVE TRIGGER MECHANISM

FIELD OF THE INVENTION

This invention is in the field of breath-actuated inhalation devices.

BACKGROUND OF THE INVENTION

Inhalation devices for delivery of therapeutic substances to the respiratory tract of a user are now in common use. Currently available methods of generating and delivering drug formulations to the respiratory tract include metered-dose inhalers, dry powder inhalers and nebulizers. The effectiveness of such devices is limited in part by the ability to coordinate release of the formulation with inhalation. Lack of coordination between inhalation velocity and release of formulation can result in deposition of formulation in areas of the respiratory tract, such as the mouth or the throat, which wastes formulation and reduces the effective concentration of formulation in the targeted portion of the respiratory tract for systemic circulation. Ideally, the formulation should be released and delivered at a point in the user's inhalation cycle such that particles of formulation are entrained in the breath and delivered into the desired portion of the respiratory tract. Devices which rely upon user-actuated release of formulation are particularly error prone. In such manually-operated devices, users frequently inhale too early or too late to effectively inspire the formulation. Problems associated with inefficient administration of a drug cannot always be compensated for by increasing the dose, as an accidental excessive dose of a therapeutic agent may have severe negative consequences.

Various breath-actuated inhalation devices have been developed in which discharge of medication is caused by a user's inspiratory effort. U.S. Pat. Nos. 5,954,047; 5,848,587; and 5,823,179. Such devices do not provide a means for coordinating release of formulation with a given inspiratory flow velocity.

A hand-held, portable breath actuated device is described in U.S. Pat. No. 5,941,240. In this device, the user inhales air through an inspiratory flow path. When the inspiratory flow meets a threshold of a preprogrammed criterion, a microprocessor sends a signal to an actuator release electrical mechanism, which in turn actuates a mechanical means of forcing formulation into the flow path.

The present invention addresses the need in the art for a simple, yet effective means of regulating the timing of formulation release in response to a user's inspiratory flow rate, and provides related advantages as well.

SUMMARY OF THE INVENTION

The present invention provides a triggering mechanism for actuating a trigger signal means upon detecting a fluid flow velocity exceeding a desired threshold. The device of the invention is capable of providing a sharp, definite signal, even in the presence of wavering or fluctuating flow velocities. Optional features of the device include provision for a delay, in which the trigger is actuated only after a preset interval following the point at which the threshold is exceeded. The trigger signal means can be operatively connected to a dispensing mechanism, whereby a transmitted signal causes a dispensing mechanism to release a volume of formulation.

The mechanism may be used in combination with a pharmaceutical inhaler, for administering a precise dosage of a pharmaceutical agent to the respiratory system of a subject or patient. The mechanism is simple, and may be disposable. Accordingly, in some embodiments, the invention provides a device for delivering an aerosolized formulation to an individual, wherein the device comprises a fluid velocity-sensitive triggering mechanism as described herein. The aerosolization devices of the invention are advantageous in that aerosol is not released below a pre-set threshold inspiratory flow rate.

In some embodiments, the triggering mechanism is configured to further provide for regulation of fluid flow rates through the mechanism. When the triggering mechanism is used in combination with an inhaler, the triggering mechanism not only controls release of formulation, but also provides greater regulation of air flow.

One aspect of the invention is a device for regulating the release and air flow of a metered dose inhaler.

Another aspect of the invention is a device for administering a metered dose of formulation, wherein said device is regulated to release the formulation over a certain range of air velocities.

An object of the invention is to provide a trigger mechanism for use in conjunction with an aerosol delivery device, wherein the trigger mechanism senses and reacts to a predetermined velocity of fluid flowing through the mechanism.

The trigger mechanism of the invention confers several advantages, among which are that it provides a simple, yet effective means for actuating an operably linked aerosolization device in response to a user's inspiratory effort.

These and other objects, advantages, and features of the invention will become apparent to those persons skilled in the art upon reading the details of the invention, as more fully described below.

BRIEF DESCRIPTION OF THE DRAWINGS

In FIG. 6A, the mechanism is in resting position.

DETAILED DESCRIPTION OF THE INVENTION

Figure 1:
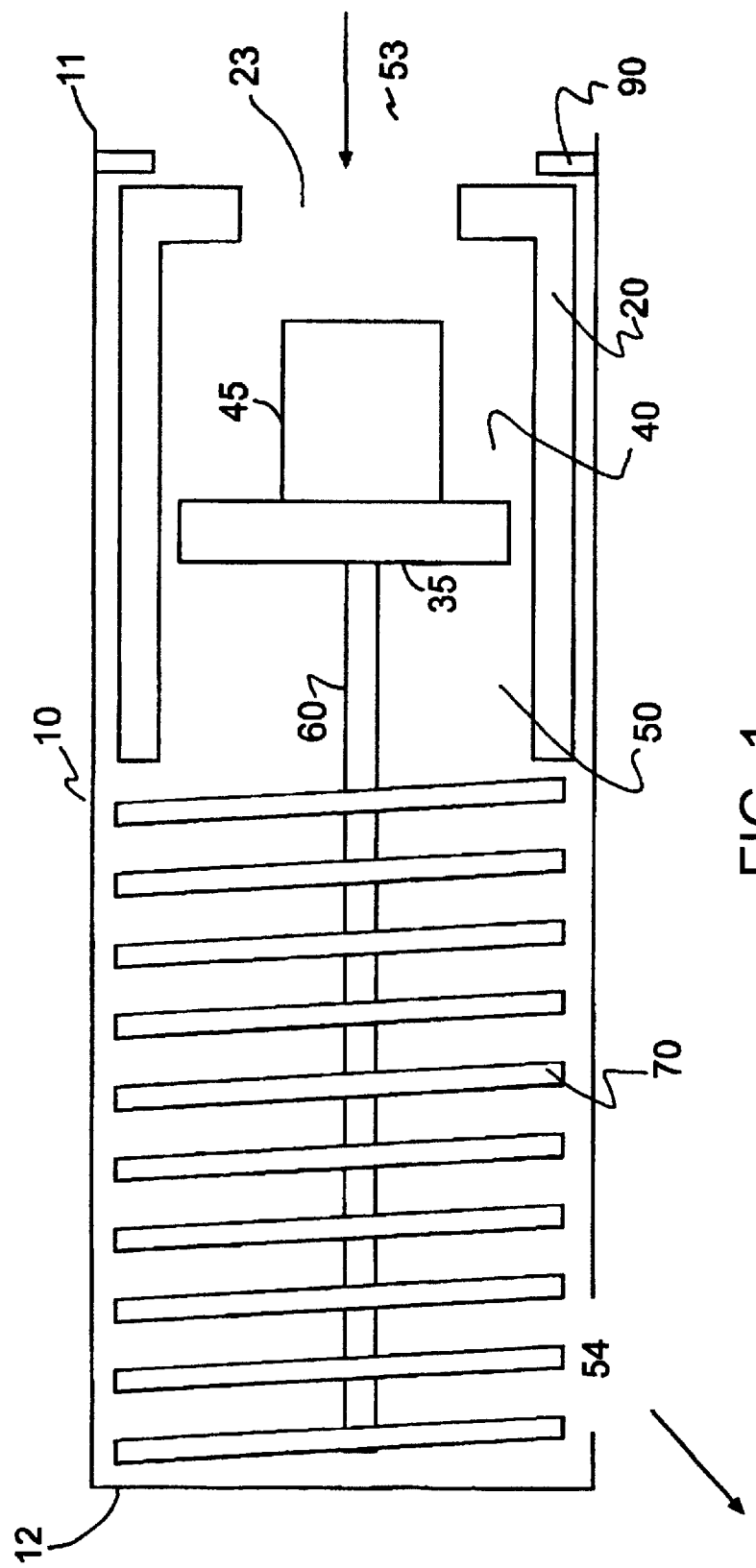
FIG. 1 is a cross section of an exemplary embodiment of the invention in operation, which is in resting position.

The invention provides a triggering mechanism which is sensitive to velocity of a fluid which passes-through the mechanism. The triggering mechanism transmits a signal to a trigger signal means, which actuates a drug release or dispensing mechanism when the flow rate exceeds a predetermined velocity. In some applications, for example when the flow rate is determined by a patient's rate of inhalation through a metered dose inhaler, the flow rate may not be constant, and may in fact fluctuate widely. In such cases, it is advantageous to employ a device which actuates firmly and definitely once the threshold is crossed, and particularly one in which a delay is imposed to ensure that the flow rate remains above the threshold for a predetermined interval before actuating. In addition, the triggering mechanism of the invention can be configured so as to regulate the fluid flow rate, to prevent it from exceeding a predetermined maximum rate.

The invention further provides inhalation devices comprising a fluid velocity-sensitive triggering mechanism as described herein. Among the advantages conferred by such devices is that a formulation is released to the user of the device only when the inspiratory flow rate reaches a certain threshold, thereby obviating problems associated with premature release of formulation from the device.

Before the present invention is described, it is to be understood that this invention is not limited to the particular methodology, devices, containers and formulations described, as such methods, devices, containers and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, reference to "an asthma attack" includes one or more of such events, and reference to "the method of treatment" and to "the method of diagnosis" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

The publications discussed above are provided solely for their disclosure prior to the filing date of the present application. Nothing herein is to be construed as an admission that the invention is not entitled to antedate such disclosure by virtue of prior invention.

Fluid Velocity-Sentitive Triggering Mechanism

The present invention provides a triggering mechanism which is sensitive to the flow rate of a fluid which passes through an fluid channel in the mechanism. By varying parameters of the triggering mechanism components, the triggering mechanism is adapted to perform one or more of the following functions: (1) detect, and optionally measure, a fluid flow rate; (2) trigger a dispensing mechanism to dispense a volume of formulation; (3) regulate fluid flow through the triggering mechanism. The triggering mechanism is particularly suited for use in an inhalation device, where the measured fluid flow is air flow inspired by the user of the device.

The triggering mechanism can be adapted to actuate a trigger signal means when the fluid flow rate is above a predetermined minimum value, $V_L$, and can also be adapted to actuate the trigger signal means below a predetermined maximum flow velocity, $V_H$.

The fluid velocity-sensitive triggering mechanism of the invention generally comprises: (1) a housing, having proximal and distal ends; (2) a piston slidably disposed within the housing, the piston having a proximal end, and a distal end which abuts a resistance means, the piston being adapted to slidably house a plug means within a fluid channel formed by an inner surface of the piston; (3) a resistance means positioned within said housing, for positioning the piston near the proximal end of the housing, wherein the resistance means prevents the piston from moving toward the distal end of the housing until fluid velocity through the channel exceeds a predetermined threshold; (4) a plug means disposed within the piston; and (5) a trigger signal means, wherein the introduction of air having sufficient velocity into the piston causes movement of the piston, resulting in actuation of the trigger signal means.

When used in conjunction with an inhalation device which comprises a dispensing mechanism operatively connected to the trigger signal means, the trigger signal means transmits a signal to the dispensing mechanism, causing release of a volume of formulation.

The piston occupies a proximal portion of the housing, while the resistance member is in a distal portion of the housing. A fluid channel is formed by an inner surface of the piston and a distal portion of the housing. Fluid flows in through the piston proximal end, and out an outlet in housing, toward a mouthpiece. Fluid flow through the fluid channel provides the driving force for movement of the piston in the direction of the fluid flow, ultimately resulting in actuation of a dispensing mechanism via a trigger signal means. The plug means provides a means for restricting air flow through the fluid channel, causing a pressure drop in the distal portion of the fluid channel, thereby hastening movement of the piston.

"Fluid" includes liquids and gases. For example, when the fluid flow is induced by inspiration of air, the triggering mechanism can be configured to actuate the trigger signal means when the air flow rate is between about 0.1 to 2.0 liters per second, or a narrower range within this range, e.g., about 0.1 to about 0.3, about 0.2 to about 0.5, about 0.1 to about 0.5, about 0.5 to about 0.75, about 0.75 to about 1.0, about 0.6 to about 0.8, about 1.0 to about 1.25, about 1.2 to about 1.5, about 1.4 to about 1.6, about 1.5 to about 1.75, about 1.6 to about 1.8, about 1.75 to about 2.0, about 1.8 to about 2.0 liters per second. This air flow rate is referred to as the "trigger flow rate." In some embodiments, the trigger flow rate is from about 0.66 to about 0.83 liters per second. In other embodiments, the trigger flow rate is from about 0.33 to about 0.4 liters per second.

"Inspiratory flow rate", as used herein, refers to a value of air flow rate measured, calculated, and/or determined based on the speed of the air passing a given point in a measuring device assuming atmospheric pressure ±5% and a temperature in the range of about 10° C. to about 40° C. The pre-determined threshold velocity, $V_L$, can be set by varying certain parameters, as explained below. $V_L$ can be varied, as desired, depending on a variety of factors, such as the age and size of the user, the physical state of the user, and the like. For example, $V_L$ might be set to a lower value for a user with reduced lung function, as compared to a user who has normal lung capacity. Reduced lung capacity can result from a variety of conditions, including, but not limited to, asthma, pneumonia, emphysema, cystic fibrosis, smoke inhalation damage, and the like. Reduced lung capacity may also be a characteristic of immature lungs, e.g., of an infant born prematurely.

In addition, the mechanism can be configured such that a maximum fluid velocity, $V_H$, is set. $V_H$ can be set in various ways, including, e.g., providing one or more vents in a sidewall of a distal portion of the housing.

Triggering Mechanism Dimensions and Configurations

In general, the dimensions of the triggering mechanism (e.g., overall length of housing; diameter of fluid channel; size and shape of venturi; flange diameter; presence, number, and shape of vents, etc.) can be varied as required or desired, and will vary according to a variety of factors (e.g., the dimensions of the inhalation device, desired flow rate, desired maximum flow rate, etc.).

The components of the trigger mechanism, such as the housing, the piston, and the plug means, are generally cylindrical. However, the triggering mechanism components need not be cylindrical. For example, if desired, any of the above components may be ellipsoidal, rectangular, square, or may take the form of a regular prism, for example a triangular, rectangular, pentagonal prism, and the like. In fact, the device need not possess any radial symmetry, as long as the piston is free to slide downstream, and as long as the fluid flow is directed through the fluid channel (e.g., substantially all of the fluid flows through the fluid channel). Additionally, it is not necessary for the device to be straight. For example, the device may be curved along an ellipsoidal, hyperbolic or parabolic arc.

Housing

In general, the housing has an overall length in a range of about 2 cm to about 10 cm, and an overall diameter in a range of about 1 cm to about 4 cm.

The housing proximal end may be completely open, or may have one or more orifices through which fluid is drawn. The housing proximal end may have one orifice which is the same size and coaxially aligned with the piston proximal end opening. In general, the housing proximal end does not impede or restrict fluid flow through the fluid channel.

At or near the housing proximal end is a retaining means for keeping the piston from exiting the housing. The retaining means may be a single projection, or a plurality of projections, or a concentric projection, in an inner surface of the housing toward the housing proximal end, or may be continuous with the housing, e.g., a rim formed at the proximal end of the housing.

The housing distal end may be coupled to a device for dispensing a formulation to a user. Disposed within the housing are a piston, a plug means, a resistance means, and a trigger signal means.

The housing may have one or more vents through its longitudinal surface, i.e, in a sidewall of the housing. These vents serve to increase resistance to prevent the air flow from attaining a predetermined upper limit, $V_H$. If present, the vents may be positioned distal to the piston distal end when piston is in "resting" position, i.e., when piston is in the proximal end of the housing. These vents are then covered, partially or completely, when the piston is drawn downstream, i.e., toward the housing distal end. Partial blockage of these vents increases the rate at which the pressure drop in the channel occurs. $V_H$ can be controlled, in part, by varying the size, shape, and number of these vents. The vents may have a roughly triangular shape, aligned longitudinally along the housing, with the narrow end toward the housing distal end. Alternatively, the vents can have a variety of other shapes, including slots, round holes, etc.

Outlet

The outlet through which fluid exits is connected, directly or indirectly, to a mouthpiece in an inhalation device. The outlet may be in the distal end surface of the housing, or in a sidewall of the housing, toward the housing distal end. The outlet may be connected to an inhalation device through a tube. The outlet may be a vent in the form of a slot or other shaped orifice, and fluid may pass through the vent to an inhalation device through a second fluid channel formed by the housing (i.e., "the first housing") and a second housing surrounding the first housing.

Plug Means and Piston

The plug means generally restricts fluid flow through the fluid channel formed by the inner surface of the piston. Restriction of fluid flow generates low pressure in a distal portion of the fluid channel, which low pressure accelerates movement of the piston toward the distal end of the housing. This accelerated movement provides the force of impact, directly or indirectly, on a trigger signal means. The plug means may be operatively connected to, and fixed in position by, the trigger signal means; or may be connected to and fixed in position by the housing proximal end. The plug means may be a solid disc, a cone, a rod, or a tapered cylinder. The plug means may also be an assembly comprising a solid disc, a cone, a rod, or a tapered cylinder and another member which serves to temporarily stop fluid flow through the channel, or which serves to fix the plug means in position. The plug means is coaxially aligned with the fluid channel, and has a cross-sectional area at its widest point which occupies at least about 75%, at least about 80%, usually at least about 90%, up to about 95%, of the cross-sectional area of the fluid channel at its narrowest point.

The piston is configured to form a fluid channel. The piston is dimensioned relative to the housing such that more than about 90%, usually more than about 95%, up to 100%, of the fluid drawn in through the proximal end of the housing toward the housing distal end passes through the fluid channel formed by the inner surface of the piston, i.e., the piston occupies more than 90% of the cross-sectional area of the housing. In general, the piston is about half the length of the housing, although the length of the piston relative to that of the housing may vary. In some embodiments, the proximal end of the piston has an orifice, which is in fluid communication with the fluid channel formed by the piston inner surface. In some embodiments, the piston forms a venturi, as described below.

In other embodiments, the piston comprises two flanges, one disposed about the piston proximal end, and the other disposed about the piston distal end. These flanges define the ends of an annular fluid reservoir which is defined by the piston outer surface and the housing inner surface, as shown in FIG. 9. The flanges may be substantially the same size, or one may have a substantially larger cross-sectional area than the other.

In some embodiments, the trigger signal means is actuated by impact of the piston on the plug means.

In these embodiments, the trigger signal means is operatively connected to the plug means, and holds the plug means in position, in coaxial alignment with an orifice in the piston proximal end. The orifice is continuous with, i.e, in fluid communication with, the channel formed by the inner surface of the piston, which accommodates the plug means. The channel formed by the inner surface of the piston is larger than the plug, thereby allowing free passage of fluid therethrough.

The plug means may be a solid disc attached to the proximal end of the trigger signal means. In a preferred embodiment, the plug means is an assembly comprising an elongate member having proximal and distal ends, and a flange disposed about the elongate member toward the elongate member distal end. The orifice is dimensioned to slidably receive the elongate member, which is coaxial with the orifice. The elongate member functions to constrict and accelerate the fluid flow through the orifice. This constriction causes a low pressure in a distal portion of the air channel, which in turn causes the piston to move toward the housing distal end. The flange is larger than the orifice, and therefore cannot pass through the orifice. Therefore, as the piston moves toward the housing distal end, the flange functions to impact the inner surface of the piston proximal end. This impact actuates the trigger signal means.

The elongate member may be roughly cylindrical, or may be conical. When conical, the wider portion of the cone is adjacent to the flange, and constriction of airflow increases rapidly as the piston travels along the elongate member. The cross-section area of the elongate member relative to that of the orifice affects the fluid flow rate through the orifice. Generally, the elongate member will occupy at least about 75%, at least about 80%, usually at least about 90%, up to about 95%, of the cross-sectional area of the orifice.

$V_L$ is controlled by the orifice size, by the resistance of the resistance means, and by the cross-sectional area of the elongate member relative to that of the orifice.

Contact between the flange and the housing proximal end inner surface also serves to temporarily diminish or stop entirely fluid flow through the triggering mechanism. Actuation of the trigger signal means causes the plug means to move toward the housing distal end, i.e., away from the piston proximal end inner surface, thereby restoring fluid flow through the orifice.

In other embodiments, the trigger signal means is actuated by impact with the distal end of the piston.

In these embodiments, the piston inner surface may be configured to form a venturi. $V_L$ can be controlled by varying the size and shape of the venturi. The venturi has a proximal throat, a constriction, and distal portion.

In these embodiments, the plug means is an assembly comprising an elongate member having proximal and distal ends, wherein the elongate member proximal end is fixed to the housing proximal end; and a plug is attached to the elongate member at the elongate member distal end. The diameter of the venturi constriction, and the size of the plug, are such that the plug occupies at least about 90% or more of the cross-sectional area of the venturi at the constriction, while allowing the plug to pass through the venturi constriction. The plug means is coaxial with the venturi formed by the piston inner surface.

At resting position, the plug is in the distal portion of the fluid channel formed by the venturi. When the fluid is air, the air channel is at atmospheric pressure. Fluid flow through the venturi and around the plug causes a low pressure within the distal portion of the venturi, which in turn causes the piston to move toward the housing distal end. Since the plug means is held in fixed position to the proximal end of the housing, movement of the piston toward the housing distal end serves to move the venturi constriction toward the plug. Entry of the plug into the constriction creates a further pressure drop in the distal portion of the fluid channel, which results in a more rapid movement of the piston toward the housing distal end.

The piston distal impacts the trigger signal means, thereby providing the signal to dispense a volume of formulation.

Fluid flow is restored when the plug traverses the venturi constriction and enters the throat of the venturi, allowing fluid to pass freely through the venturi constriction.

Resistance Means

The resistance means can be any means that provides sufficient resistance to the movement of the piston toward the housing distal end, so that the piston's movement results in actuation of trigger signal means only at a predetermined fluid velocity threshold. The resistance means exerts a force, F, on the piston, urging it toward the housing proximal end. The force provided by the resistance means can be varied so as to set $V_L$. In general, the force exerted on the piston by the resistance means is in a range of about 1 g to about 40 g, from about 2 g to about 20 g, or from about 5 g to about 10 g.

The resistance means is generally configured so as to accommodate the trigger signal means, i.e., be disposed around the trigger signal means. For example, the resistance means may be disposed about the inner perimeter of the housing, or may have a channel through which the trigger signal means extends. The resistance means must be configured so as not to impede the flow of fluid through the fluid channel.

In some embodiments, the resistance means is a spring. The spring has a tension generally in the range of about 1 g to about 40 g, from about 2 g to about 20 g, or from about 5 g to about 10 g. The spring could be a single coil, disposed about the inner perimeter of the housing, or could be a plurality of coils disposed about the inner perimeter of the housing.

Other resistance means can be used in the triggering mechanism. For example, the resistance means can be a cylinder having a channel therethrough to accommodate trigger signal means. The cylinder could be reversibly collapsible, thereby providing the required resistance to the piston. The cylinder material itself could provide the resistance, or, alternatively, the cylinder could be filled with a substance, such as a fluid or a gel, which would provide the requisite resistance.

Trigger Signal Means

The trigger signal means is any means capable of transmitting a signal provided by impact of the plug, or alternatively, of the distal end of the piston. The signal transmitted can (1) provide information about the fluid flow rate to a means for recording such information; and/or (2) actuate a formulation dispensing mechanism; and/or (3) actuate a feedback means for regulating the fluid flow rate.

The trigger signal means can be operatively connected to, and actuated by, the plug means, or, may be actuated by impact with the piston. When operatively connected to a plug means wherein the plug means is a flange, the trigger signal means may be rigidly connected, directly or indirectly, to the flange.

When actuated by impact with the piston, the trigger signal means need not be, and indeed preferably is not, in direct contact with the piston until the fluid flow rate has exceeded the predetermined threshold value.

The trigger signal means can be a single entity or a plurality of interacting entities. The trigger signal means may be a mechanical means or an electrical means. As one non-limiting example, the trigger signal means may comprise a substantially stiff rod. As another non-limiting example, the piston could cause the closure of an electrical switch that electrically actuates the trigger mechanism to dispense the drug.

The trigger signal means may act directly or indirectly on a formulation dispensing means.

Regulating Means

The trigger mechanism may be configured to comprise features which allow regulation of air flow through the mechanism. For example, as described above, the housing may have one or more vents, in a sidewall of the housing toward the housing distal end, which serve to limit $V_H$.

Another way to regulate air flow is to require an initial volume of fluid to pass through the mechanism before the piston begins to move. A combination of ambient atmosphere and air inside the reservoir is inhaled by the user. A portion of the initial volume of fluid may be provided in an air reservoir which is in fluid communication with the fluid channel, e.g., through a port through the piston. The air reservoir may be in the form of an annular space between the piston and the housing, where the annular space is formed by an outer surface of the piston and an inner surface of the housing. The air reservoir can be in any configuration, such as a tube disposed in a spiral configuration about the piston. The volume of fluid contained within the air reservoir must be reduced sufficiently before the piston will begin moving. The size of the port will determine to some extent how rapidly the volume of air in the reservoir is evacuated. Increasing the diameter of the port decreases the effective initial volume.

Trigger Mechanism Materials

Any material can be used for the trigger mechanism and its components. Suitable materials are those that do not react with the fluid flowing through the mechanism. Preferred are materials that are lightweight. In some cases, the trigger mechanism will be used in conjunction with a device intended for single use applications. Accordingly, when intended for single-use applications, the materials should be inexpensive, as well as lightweight.

Exemplary materials include, but are not necessarily limited to, polymers, metals, metal alloys, glasses, laminates of hydrophilic polymers and hydrophobic polymers, multi-laminates or polymer, metals, and/or glasses; and the like.

Specific exemplary polymeric materials include, but are not necessarily limited to, homopolymers and copolymers of vinyl acetate (e.g., ethylene vinyl acetate copolymer); homopolymers and copolymers of acrylates (e.g., poly(methyl)methacrylate (PMMA), polyethylmethacrylate, ethylene glycol dimethacrylate, ethylene dimethacrylate and hydroxymethyl methacrylate); polyurethanes; polyethylenes; polyvinylchlorides; polycarbonates; polyamides; polysulfones; polyesters; polyimides; halogenated polymers (e.g., polytetrafluoroethylene (PTFE), polyvinyl fluoride, polychlorotrifluoroethylene, copolymers tetrafluoroethylene and hexafluoropropylene; PFA, and the like); polyolefins (e.g., high density polyethylene (HDPE), low density polyethylene (LDPE), linear low density polyethylene (LLDPE), polypropylenes, and the like); polystyrenes; nylons; urethanes; homopolymers and copolymers of acrylonitrile (e.g., acrylonitrile-butadiene-styrene polymer, styrene acrylonitrile, polycarbonate-acrylonitrile-butadiene-styrene; and the like); polyvinylpyrrolidone; 2-pyrrolidone; polyacrylonitrile butadiene; cellulose acetate; polyethylene terephtholate; polymethylpentene; polyisobutylene; polymethylstyrene; polyvinylidine chloride and homopolymers and copolymers of polyvinylidine chloride (e.g., polyvinylchloride-acrylic copolymers); PEBAX™; HYTRE™; and other similar compounds known to those skilled in the art. Further exemplary polymers are described in *Plastics Materials* 6$^{th}$ ed., May 1995, J. A. Brydson, Butterworth-Heinemann, publishers.

Materials for the piston may further include carbon steel, chromium-molybdenate alloys, titanium, and the like.

Materials for the spring can be selected according to the desired design, e.g., to provide for compression strength. Exemplary materials for use in the spring include, but are not necessarily limited to, metals (e.g., stainless steel wire, parylene-coated or Teflon-coated stainless steel), metal alloys), polymers (e.g., particularly polymers of relatively high modulus, e.g., carbon fiber,) and the like.

Exemplary Specific Embodiments of the Triggering Mechanism of the Invention

Specific exemplary embodiments of the triggering mechanism of the invention will now be described in terms of the figures. Turning now to FIG. 1, an embodiment of the invention is depicted in isolation: in operation, the trigger mechanism would be positioned at one end of a pulmonary drug delivery system, such that fluid passes through the trigger mechanism, toward the user. FIG. 1 shows the trigger mechanism of the invention "at rest", i.e., the air in the fluid channel is at atmospheric pressure. Housing 10 has proximal end 11 and distal end 12, and an outlet 54 to inhalation device (not shown), and contains within it piston 20 comprising an orifice 23 in fluid communication with channel 50, which is formed by inner surface of piston 20. Elongate member 45 of plug assembly 40 is dimensioned to fit within orifice 23 without sealing the orifice 23, although flange 35 does substantially constrict the orifice. Elongate member 45 and flange 35 are supported in place by trigger signal means 60, depicted here as a solid rod. Piston 20 is held in place against the air flow by resistance means 70, shown here as a coiled spring. Retaining projection 90, which may be a concentric flange, a projection, or a plurality of projections, retains piston 20 within the housing, and permits spring 70 to be pretensioned.

Figure 2:
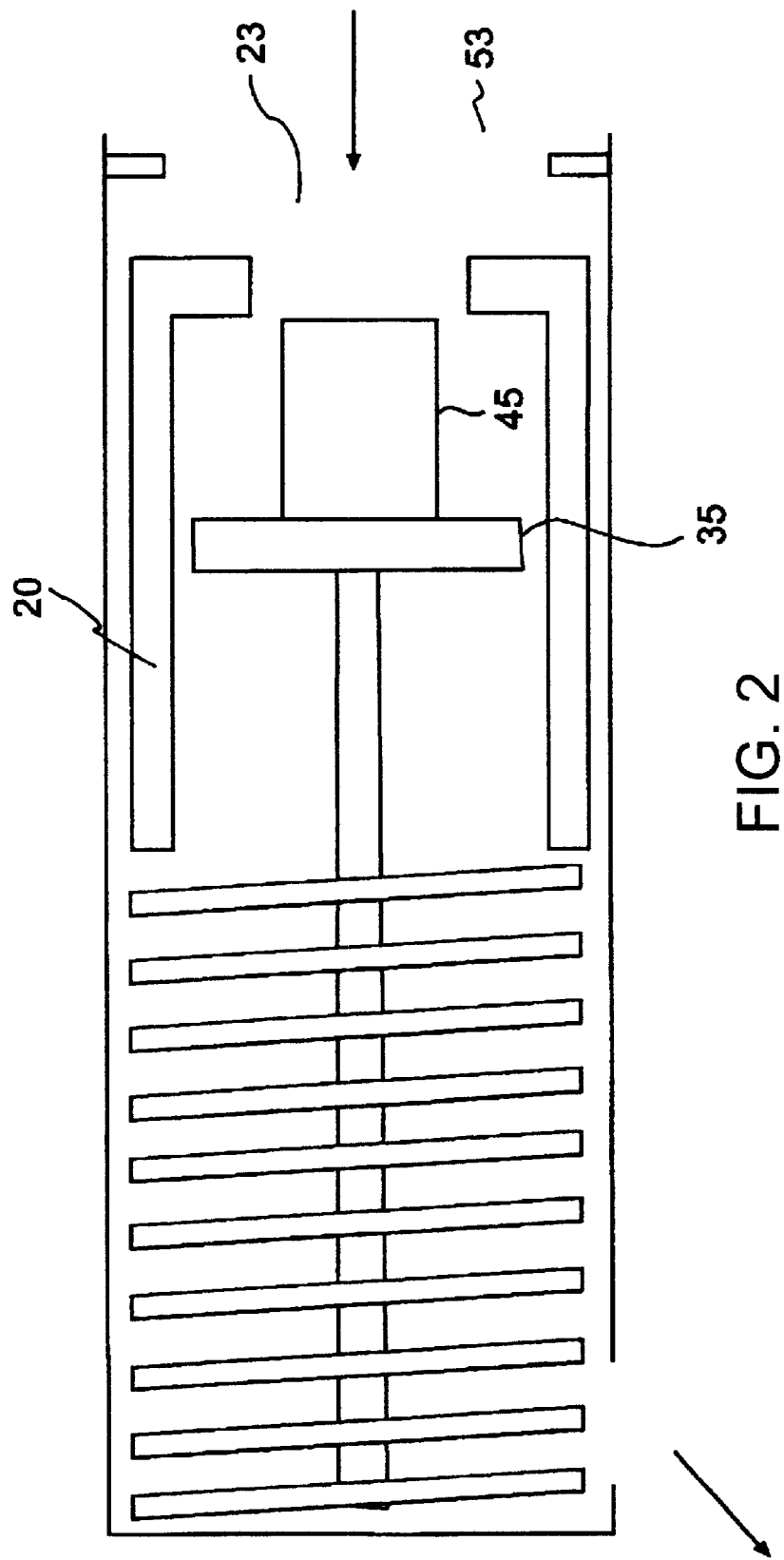
FIG. 2 shows the device as shown in FIG. 1 at the point at which air flow has overcome spring resistance, and has moved the piston downstream to the plug.

When air (or other gas or liquid) is drawn into inlet 53 of channel, through piston orifice 23 and further through channel 50, piston 20 remains essentially at rest, held in place by resistance means 70 until air pressure is sufficient to overcome the resistance force, at which point the piston begins to move downstream (i.e., toward housing distal end 12), thereby compressing spring 70. As the piston 20 and orifice 23 approach elongate member 45 as shown in FIG. 2, the airflow through orifice 23 becomes more constricted, causing the airflow to accelerate piston 20 against flange 35.

Figure 3:
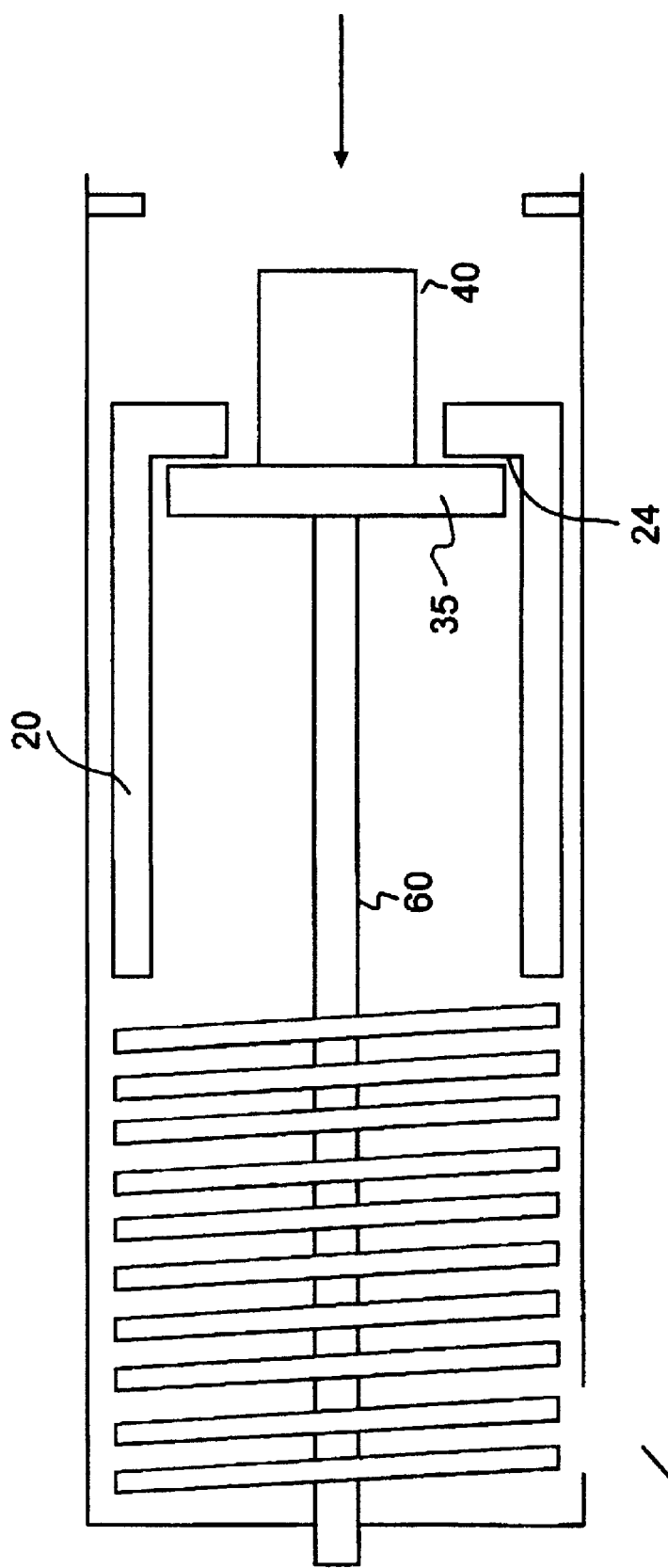
FIG. 3 shows the device as shown in FIG. 1 at the moment in which the piston impacts the plug assembly flange, actuating the trigger signal means.
Figure 4:
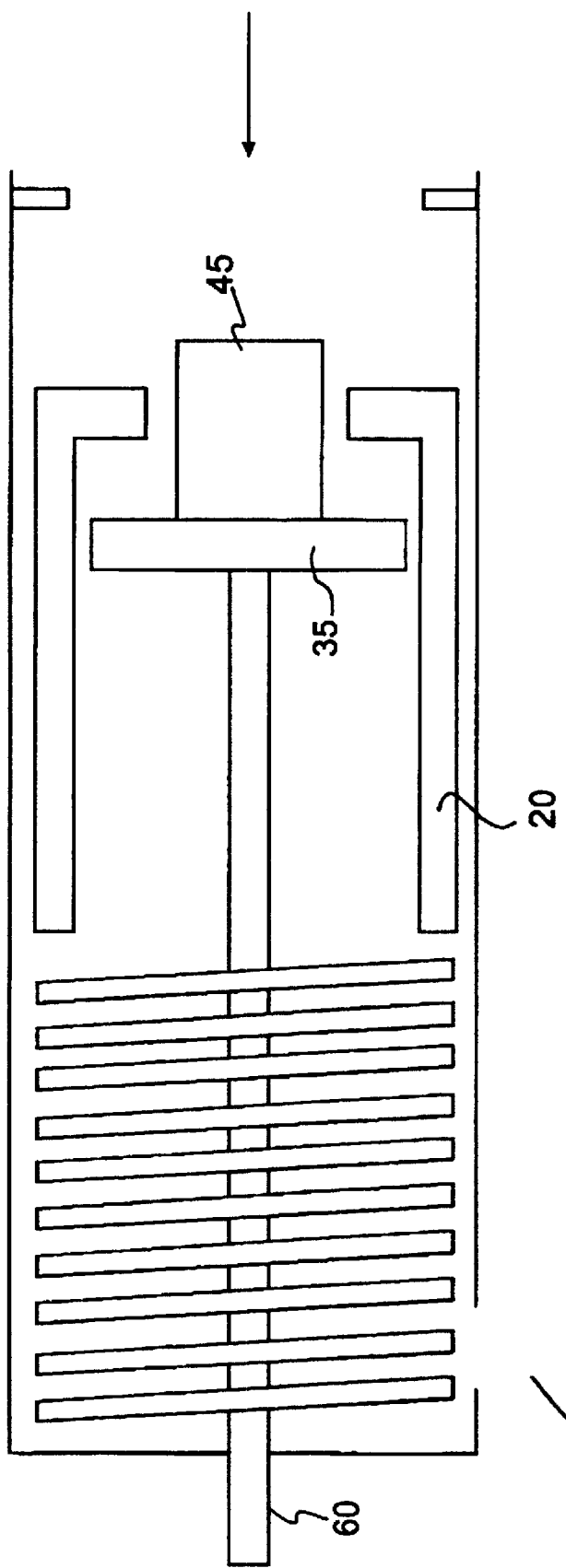
FIG. 4 shows the device as shown in FIG. 1 after actuation of the trigger signal means, wherein movement of the trigger signal means allows re-establishment of air flow through mechanism.

The impact of piston 20 against flange 35 urges trigger signal means 60 downstream, actuating the dispensing mechanism (not shown), as depicted in FIG. 3. Piston 20 proximal end inner surface 24 may seal against flange 35, in which case the airflow will contribute to the force against the trigger signal means 60; however, this is optional. Once actuated, the trigger signal means allows plug assembly 40 to move (or causes it to move) downstream, thus permitting an increased (or resumed) airflow through orifice 23, as shown in FIG. 4. Piston 20 is prevented from continuing downstream either by a restraining means, such as a flange or projection inside housing 10, or, as shown here, by the increasing resistance of the resistance means 70, for example a spring.

Figure 5:
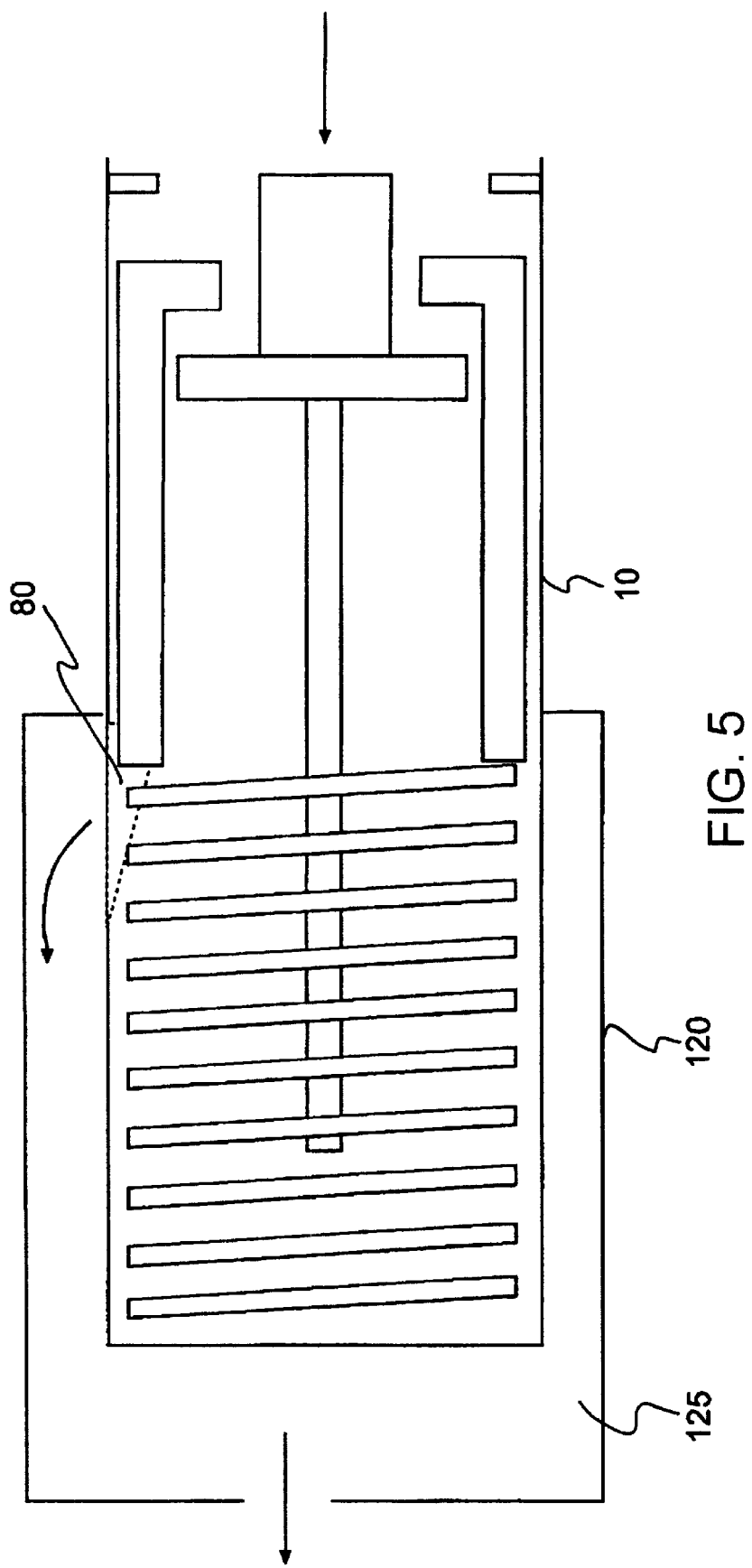
FIG. 5 shows a further embodiment of the device as shown in FIG. 1 in which a shaped vent in a sidewall of the housing allows regulation of air flow by establishing an upper velocity limit.

FIG. 5 shows a variation in which housing 10 is provided with one or more shaped vents 80, which open to a second housing 120 which surrounds first housing 10, forming a second air channel 125. Once the trigger signal means has been actuated, the piston continues to move downstream, partially covering the shaped vent(s) 80. Flow velocity is limited to an upper value, $V_H$, in part by the number and shape of these vents.

Figure 6:
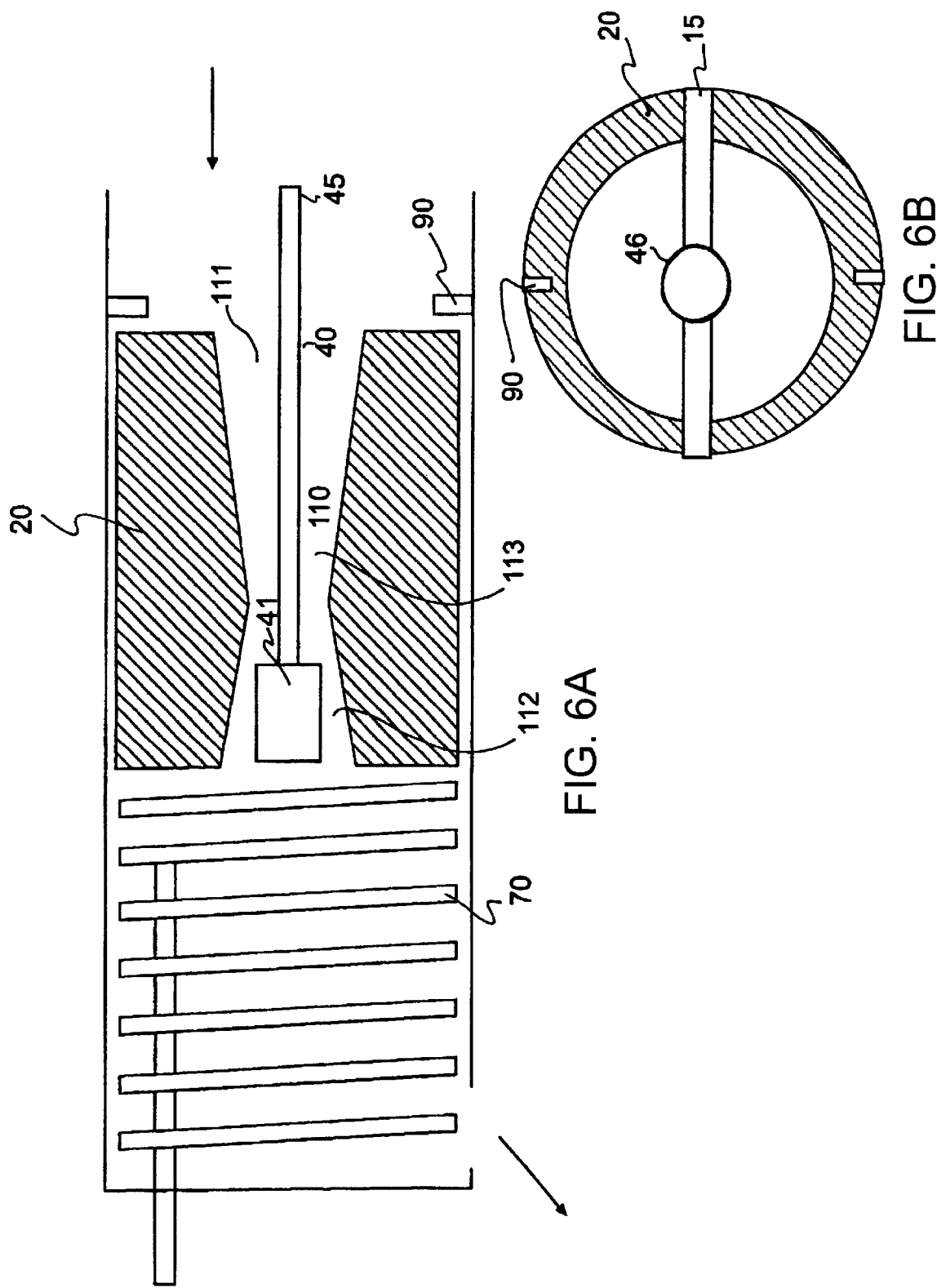
FIG. 6A is a cross section of another exemplary embodiment of the invention, having a piston in the form of a sliding venturi.
FIG. 6B shows a top view of the proximal end of the embodiment shown in FIG. 6A.

FIG. 6A depicts another embodiment of the invention, in which piston 20 forms a venturi 110, having throat 111, distal portion 112, and constriction 113 dimensioned to admit plug 41 of plug assembly 40, which is fixed in position by elongate member 45. Piston 20 is positioned against retaining projection 90, and held in place by pretensioned spring 70. The venturi 110, and plug 41 are dimensioned and positioned such that at the desired flow rate, air pressure urging piston 20 toward housing distal end is balanced by the resistance force from spring 70. Plug 41 is positioned to reside in distal portion 112 of venturi 110 when at rest, i.e., when air pressure in fluid channel is at atmospheric pressure. FIG. 6B is a view of the proximal end of the embodiment shown in FIG. 6A. Retaining projections 90 retain piston 20 in housing 10, while plug assembly is held into place by attachment between elongate member proximal end 46 and retaining member 15 continuous with housing proximal end.

Figure 7:
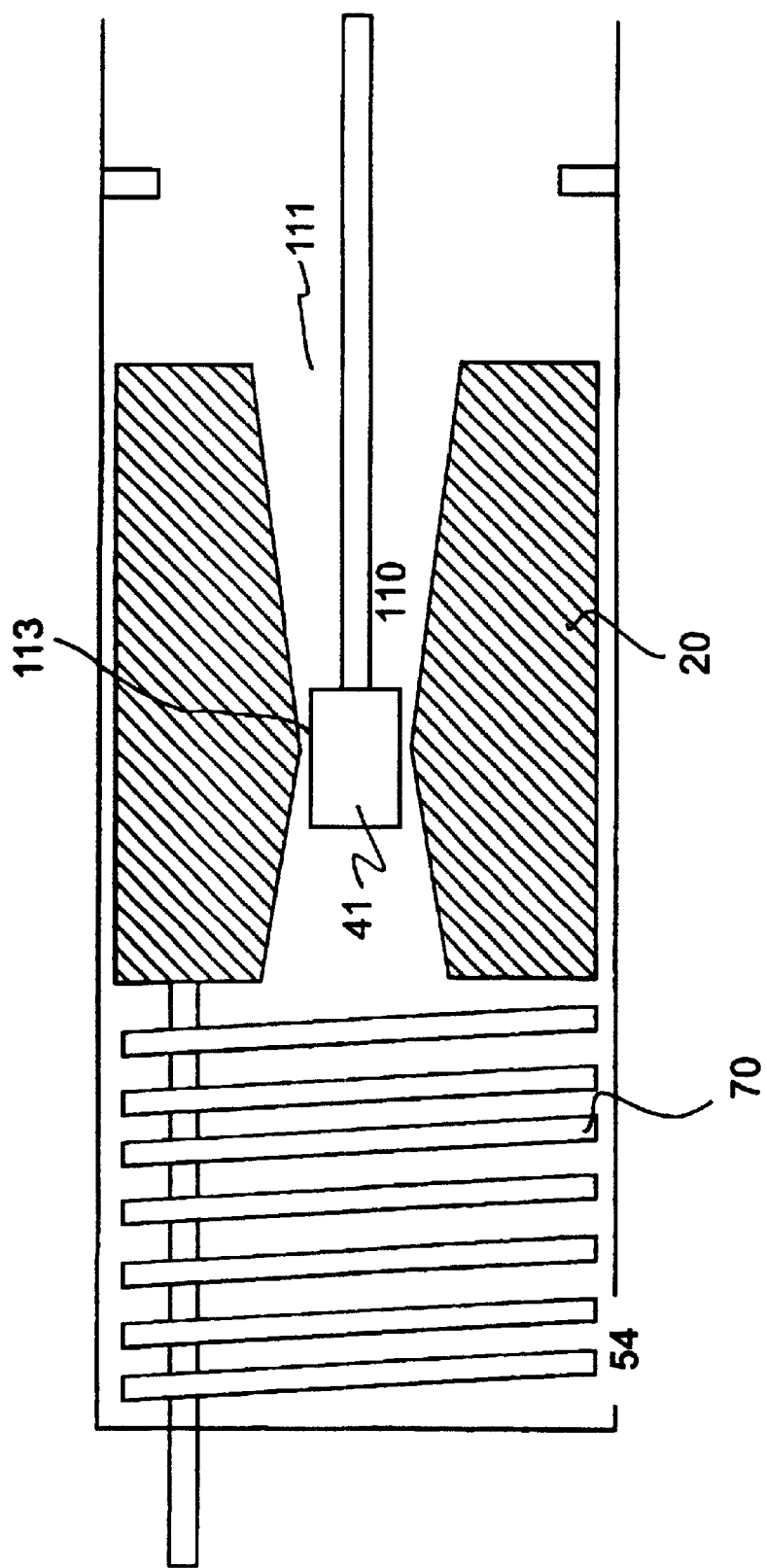
FIG. 7 shows the device as shown in FIG. 6 at the point of trigger actuation.
Figure 8A:
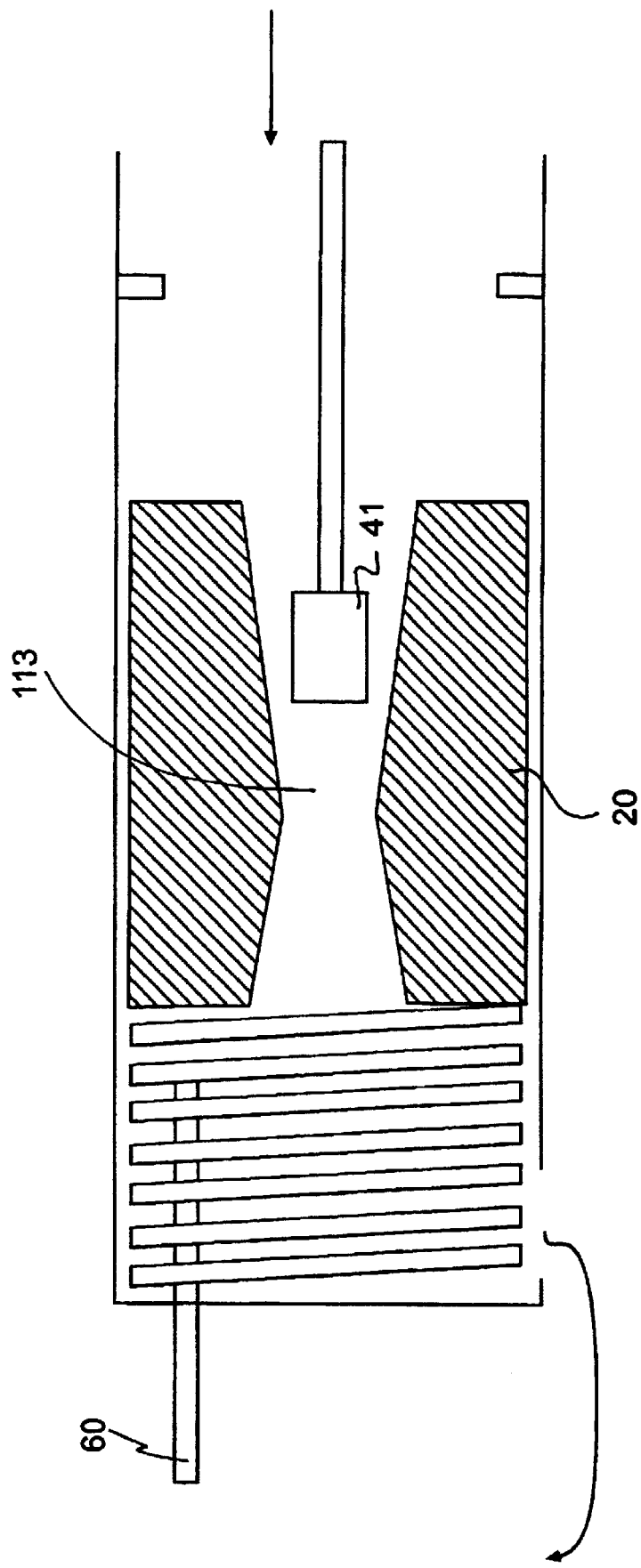
FIG. 8A shows the device as shown in FIG. 6 following actuation, regulating the air flow.
Figure 8B:
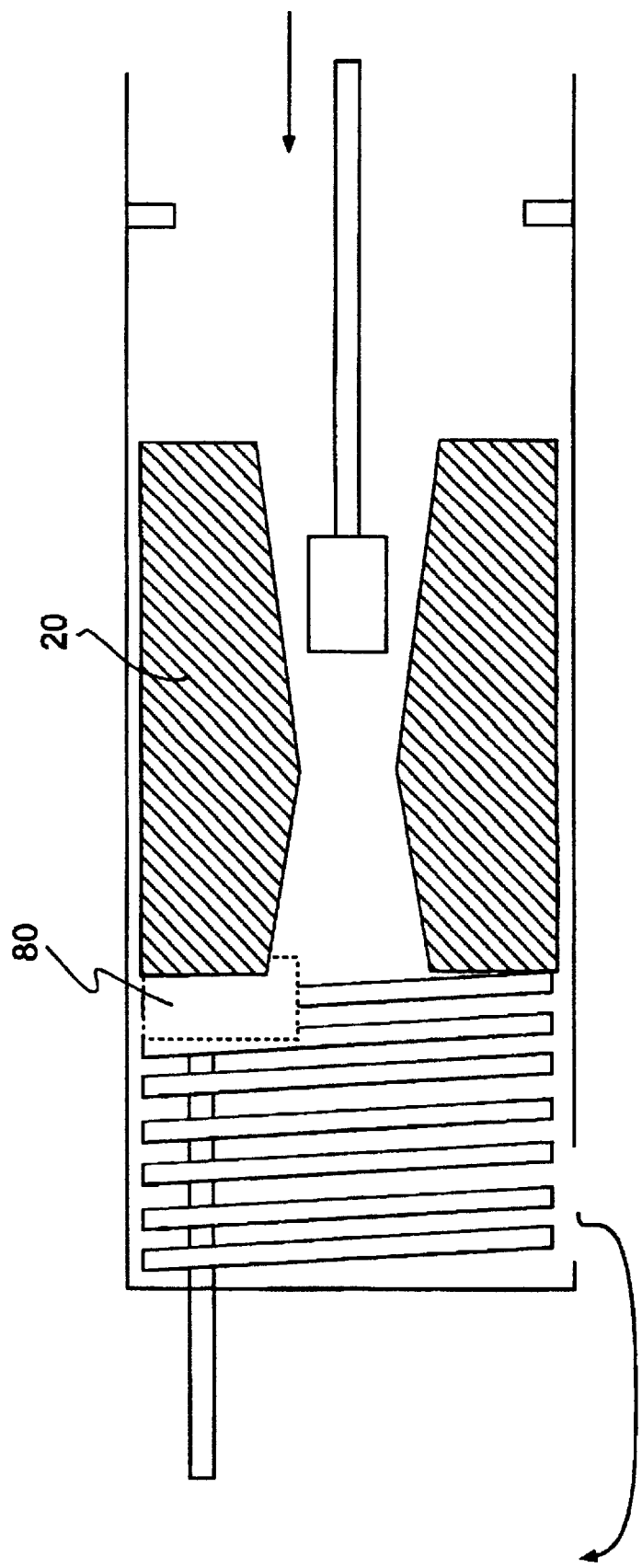
FIG. 8B shows the device with regulatory slots, which serve to set an upper velocity limit.

In operation, as shown in FIG. 7, air is drawn into throat 111 of venturi 110 (as indicated by arrow), passes through venturi 110, further through distal portion of fluid channel, and exits through an outlet 54 in housing 10. The resulting pressure urges piston 20 downstream against the counterbalancing force from spring 70. The spring force is selected so that it is overcome by the pressure resulting from air flow at the desired velocity, e.g. $V_L$, the triggering velocity. Piston 20 moves gradually until plug 41 enters constriction 113 between the venturi throat 111 and venturi distal portion 112, thereby restricting airflow, which causes a rapid pressure drop in distal portion of fluid channel. The sudden drop in pressure accelerates piston 20 downstream to impact with trigger signal means 60, which impact causes the trigger signal means to actuate a dispensing mechanism (not shown). As shown in FIG. 8A, actuation causes trigger signal means 60 to move downstream, out of the way of piston 20, which may then proceed further downstream, whereupon plug 41 no longer occupies venturi constriction 113, thereby re-establishing fluid flow. Piston 20 now is free to continue to move downstream, whereupon, as shown in FIG. 8B, vents 80, in housing sidewall are partially covered by the piston 20. This partial blockage of the vents causes an increased pressure drop with increasing flow rate, thereby placing an upper limit on $V_H$.

Figure 9A:
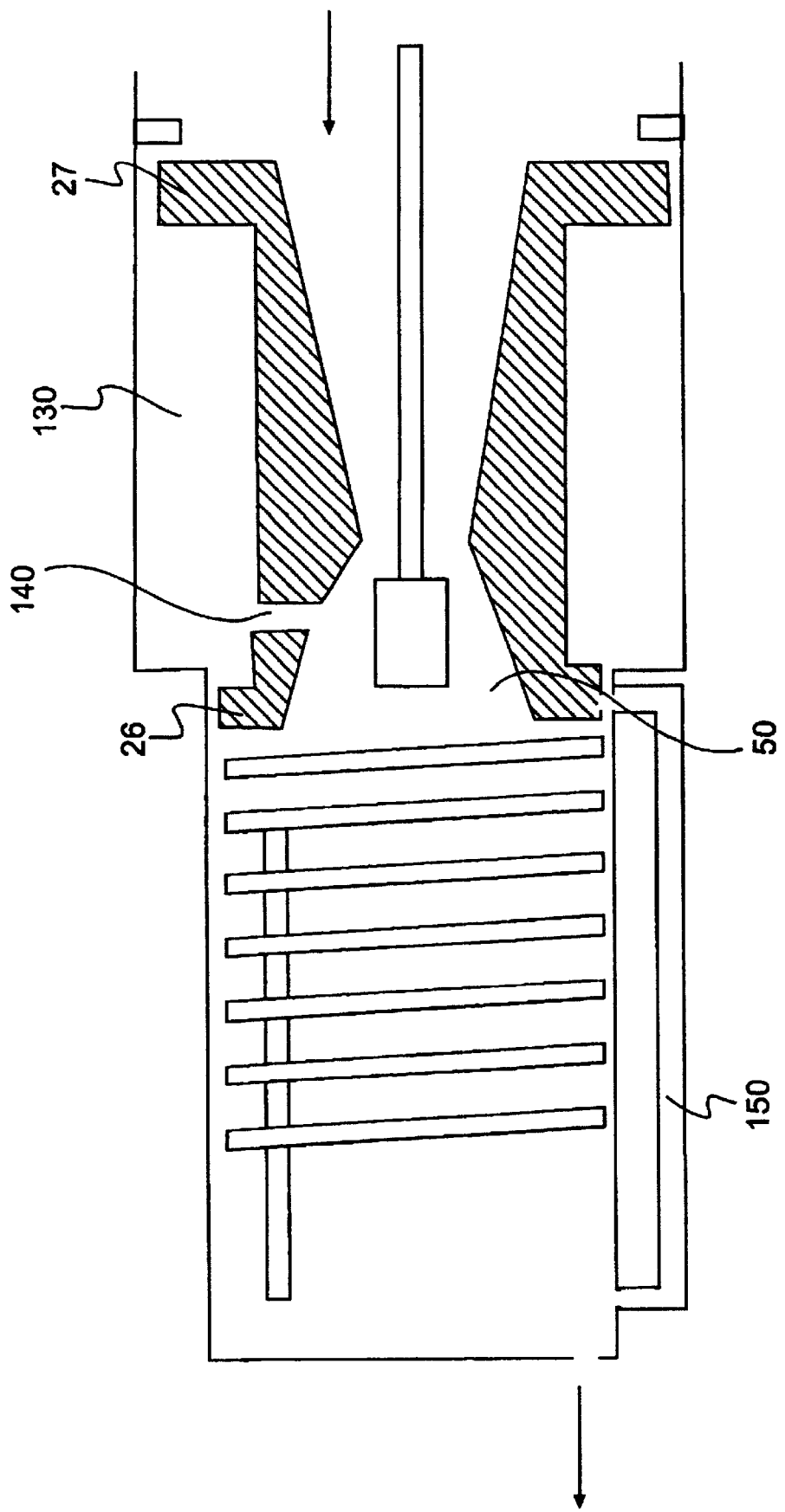
FIG. 9A is a cross section of a further embodiment of the invention, illustrating a delay configuration.
Figure 9B:
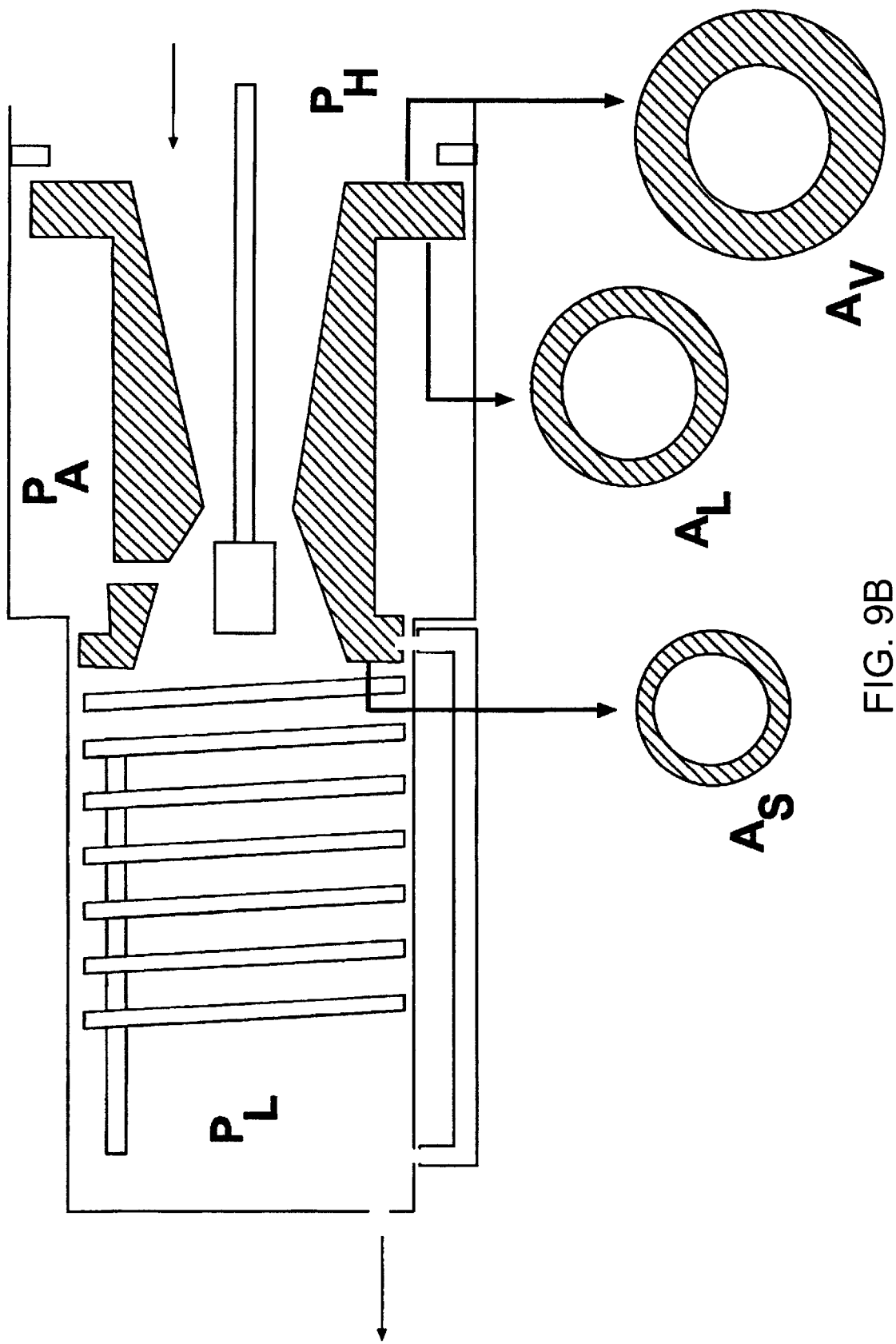
FIG. 9B illustrates the pressures in various portions of the exemplary mechanism of FIG. 9A, as well as the cross-sectional areas of particular portions of the piston.

FIGS. 9A and 9B show another embodiment of the invention, configured to delay actuation of the device until a preset time after the desired air flow velocity is attained. The device shown in FIGS. 9A and 9B differs from that depicted in FIGS. 6–8 in the provision of an air reservoir 130 which communicates with central air channel 50 through port 140, and optionally also through bypass 150. Reservoir 130 is shown here as an annular space around piston 20, which here is provided with flanges 26 and 27 to seal the expanded air reservoir space. The device operates as described for FIGS. 6–8 above, but motion of piston 20 downstream is delayed by the time required for the air in reservoir 130 to pass through port 140 in the piston and into the inner air channel 50. As shown here, the housing is provided with a bypass 150 (shown here as a slot in the side of the housing), which permits reservoir 130 to be emptied rapidly once the piston has moved far enough downstream for flange 26 to travel past the opening of the bypass. This rapid evacuation of the air reservoir accelerates piston downstream movement.

In this embodiment, the air reservoir is initially at atmospheric pressure, $P_H$, as shown in FIG. 9B. The annular volume must decrease to a value, $P_A$, such that the force, F, exerted by the resistance means is exceeded, allowing the piston to move downstream, i.e., $$(P_H)(A_V)-[(P_A)(A_L)+(P_L)(A_S)]>F.$$

Figure 10:
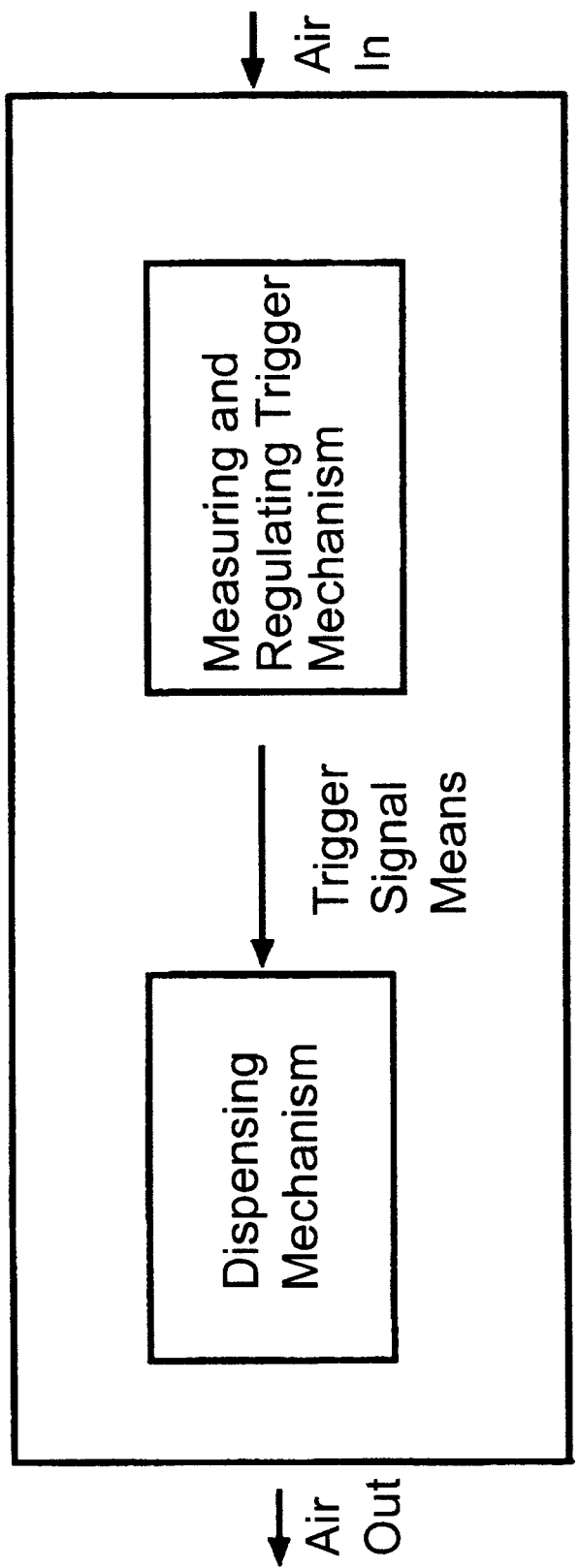
FIG. 10 is a schematic representation of a trigger mechanism of the invention operably connected to a dispensing mechanism via a trigger signal means.

The trigger mechanism of the invention is shown schematically in FIG. 10, in operable linkage with a trigger signal, a dispensing mechanism, and mouthpiece.

Further Variations

The triggering mechanism can be adapted to include a measuring means for measuring a fluid velocity through the fluid channel. The measuring means may additionally have a readout, such as a digital readout, which can be read by the user or a clinician, and may also provide a signal, such as a visual or an auditory signal, to the user, when a fluid velocity has been reached. The measuring means can further comprise a data storage means to store the measured flow rate.

Inhalation Devices Comprising a Fluis Velocity-Sensitive Trigering Mechanicsmi

The trigger mechanism of the invention may be used in conjunction with or as part of any known inhalation device, including metered dose inhalers, and dry powder inhalers. The trigger mechanism may also be used in conjunction with, or as a part of, a ventilation device for ventilating a patient not capable of voluntary breathing. The trigger mechanism may also be used in conjunction with an inhalation device connected with a face mask for use in delivering formulation to a user with reduced lung function.

Examples of preferred inhalation devices for use in conjunction with the trigger mechanism of the present invention are those described in U.S. Pat. Nos. 5,622,162; 5,608,647; 5,934,272; 5,915,378; 5,906,202, incorporated herein by reference.

An exemplary method for using the aerosol delivery device is as follows. The user (also referred to herein as "individual" or "patient") inhales through the mouth from a tubular channel. An inhalation velocity above a predetermined $V_L$ actuates the trigger mechanism, which is operatively connected to dispensing mechanism of inhalation device, thereby effecting release of formulation into the respiratory tract of the user.

A device of the invention can be similarly used to deliver a drug to the respiratory tract by nasal delivery. For example, the mouthpiece and opening are suitably modified to provide for delivery by nasal inhalation. Thus, the patient places the opening of the modified device into his nostril and, after inhalation, a dose of the drug is delivered to the respiratory tract of the patient in a manner similar to that described above.

In general, aerosol delivery devices of the invention comprise (a) a device for holding one or a plurality of formulation-containing containers, preferably a disposable container; (b) a mechanical means for forcing the contents of a container through a nozzle or a porous membrane; and (c) a triggering mechanism of the present invention. The delivery device of the present invention further provides (d) a means for controlling the inspiratory flow profile, (e) a means for controlling the volume in which the drug or diagnostic agent is inhaled, (f) a switch for automatically releasing or firing the mechanical means to release a determined volume of aerosol and aerosol-free air after the inspiratory flow rate and/or volume reaches a predetermined point. Preferably, the dispenser further comprises (g) a means for holding and moving one package after another into a drug release position so that a new package is positioned in place for each release of drug, and (h) a source of power, e.g., spring, or conventional batteries or other source of electric power.

When administering a formulation comprising a drug or diagnostic agent using the device of the present invention, the entire dosing event can involve the administration of anywhere from 10 μl to 10,000 μl, and generally involves the administration of approximately 10 μl to 1,000 μl of formulation. Very small amounts of drug or diagnostic agent (e.g., nanogram amounts) may be dissolved or dispersed within a pharmaceutically acceptable, liquid, excipient material to provide a liquid, flowable formulation which can be readily aerosolized. The large variation in the amounts that might be delivered are due to different drug potencies and different delivery efficiencies for different devices, formulations, and patients.

The entire dosing event can involve several inhalations by the patient with each of the inhalations being provided with drug or diagnostic agent from the device. For example, the device can be programmed so as to release the contents of a single container or to move from one container to the next on a package of interconnected containers. Such dosing events comprised of multiple inhalations can be used to, for example, titrate an amount of insulin delivered to adjust the patient's blood glucose level. Delivering smaller amounts from several containers can have advantages. Since only small amounts can be delivered from each container and with a single administration, even a complete failure to deliver drug with a given single dose is not of great significance and will not seriously disturb the reproducibility of the dosing event with multiple administrations.

In addition to the target area of the respiratory tract, (1) drug potency, (2) delivery efficiency, and (3) sensitivity of the patient to the drug or diagnostic agent must be taken into consideration. The present invention makes it possible to vary dosing over time if sensitivity changes and/or if user compliance and/or lung efficiency changes over time.

Based on the above, it will be understood that the dosing or amount of drug or diagnostic agent (and in particular the volume of aerosolized drug) actually released from the device can be changed based on the patient's responsiveness to therapy or the amount (or adequacy of the amount) of diagnostic agent delivered. For example, where a respiratory drug is delivered according to the invention, the most immediately prior monitoring event wherein the inspiratory flow of a patient's inhalation could be measured. Variations in doses can be calculated by, for example, monitoring the effect of one or more lung function parameters in response to known amounts of respiratory drug released from each container and delivered to the patient.

Additional information regarding dosing with drugs can be found within "Harrison's Principles of Internal Medicine" (most recent edition) and the "Drug Evaluation Manual", 1993 (AMA—Division of Drugs and Toxicology) (both pub. by McGraw Hill Book Company, NY), incorporated herein by reference to disclose conventional information regarding dosing of drugs and in particular respiratory drugs as well as other useful drugs, diagnostic agents, and formulations.

Although described herein in terms of use with a metered dose inhaler, the device of the invention may also be used in other contexts, e.g., to trigger an alarm in a gas or liquid delivery system.

While the present invention has been described with reference to the specific embodiments thereof, it should be understood by those skilled in the art that various changes may be made and equivalents may be substituted without departing from the true spirit and scope of the invention. In additions, many modifications may be made to adapt a particular situation, material, device, mechanism, process, process step or steps, to the objective, spirit and scope of the present invention. All such modifications are intended to be within the scope of the claims appended hereto.

What is claimed is:

1. A triggering mechanism comprising:
   a) a housing, having proximal and distal ends;
   b) a piston slidably disposed within said housing, said piston comprising proximal and distal ends and an orifice, wherein said piston is adapted to slidably house a plug means, wherein said housing and an inner surface of said piston together define a fluid channel having an inlet in said piston proximal end, and an outlet in said housing distal end;
   c) a resistance means which abuts said piston distal end, for positioning said piston near the proximal end of said housing, wherein said resistance means prevents said piston from moving toward the distal end of said housing until air velocity passing through said piston orifice exceeds a predetermined threshold;
   d) a plug means disposed within said piston; and
   e) a trigger signal means,
   wherein elements (a) through (e) are configured in such a way that passage of air having sufficient velocity through said piston orifice moves said piston toward the housing distal end, thereby actuating said trigger signal means.

2. The mechanism of claim 1, wherein said piston comprises an orifice in piston proximal end, and said plug means is operatively connected with said trigger signal means, and is coaxially aligned with said orifice, said plug means comprising an elongate member having proximal and distal ends, and a flange disposed about said elongate member distal end.

3. The mechanism of claim 2, wherein said piston orifice and said elongate member are dimensioned such that a pressure drop sufficient to accelerate said piston toward said housing distal end is generated in said fluid channel when said piston orifice engages said elongate member.

4. The device of claim 2, wherein said trigger signal means comprises a solid member connected rigidly to said plug means, wherein said trigger signal means transmits the impact of said piston on said flange.

5. The device of claim 4, further comprising:
   a trigger retaining means capable of maintaining said solid member in position until actuated.

6. The device of claim 5, wherein said trigger retaining means allows said solid member and said plug means to move downstream when actuated.

7. The device of claim 6, further comprising:
   an outer housing, encasing said housing without obstructing said fluid channel, said outer housing providing a second fluid channel between said housing and said outer housing, wherein said housing further comprises a vent between said housing and said outer housing.

8. The device of claim 7, wherein said vent is positioned to be partially covered by a piston sidewall following actuation, wherein said vent is dimensioned to provide for a substantially constant air velocity.

9. A triggering mechanism comprising:
   a) a housing, having proximal and distal ends;
   b) a piston slidably disposed within said housing, said piston comprising proximal and distal ends, wherein said piston is adapted to slidably house a plug means, wherein said housing and an inner surface of said piston together define a fluid channel having an inlet in an orifice in said piston proximal end, and an outlet in said housing distal end;

c) a resistance means which abuts said piston distal end, for positioning said piston near the proximal end of said housing, wherein said resistance means prevents said piston from moving toward the distal end of said housing until air velocity passing through said piston orifice exceeds a predetermined threshold, d) a plug means disposed within said piston and operatively connected to a trigger signal means, said plug means comprising:
   i) an elongate member aligned with said piston orifice, said plug means dimensioned to fit within said orifice without sealing said orifice; and
   ii) a flange disposed about said elongate member toward said elongate member distal end, said flange being larger than said piston orifice; and e) a trigger signal means, wherein passage of air having sufficient velocity through said piston orifice moves said piston toward the housing distal end, engaging said plug means in said orifice, until said flange impacts said piston proximal end inner surface, thereby actuating said trigger signal means.

10. A triggering mechanism comprising:

a) a housing having proximal and distal ends;

b) a piston slidably disposed within said housing, said piston having an inner surface which defines a venturi, wherein said housing and said venturi together define a fluid channel having an inlet in the piston proximal end, and an outlet in said housing distal end, and further wherein said venturi comprises a throat, a constriction, and a distal portion;

c) a resistance means which abuts said piston distal end, for positioning said piston near the proximal end of said housing, wherein said resistance means prevents said piston from moving toward the distal end of said housing until air velocity passing through said fluid channel exceeds a predetermined threshold;

d) a plug assembly disposed within said venturi, coaxially aligned with said inlet, said plug assembly comprising a plug dimensioned to fit within said venturi constriction without sealing same; and e) a trigger signal means;

wherein the introduction of air having sufficient velocity into said inlet of said fluid channel moves said piston toward housing distal end until said piston engages said plug and contacts said trigger signal means.

11. The mechanism of claim 10, wherein said venturi constriction and said plug are dimensioned such that a pressure drop sufficient to accelerate said piston toward said housing distal end is generated when said constriction engages said plug.

12. The mechanism of claim 11, further comprising:
an outer housing, encasing the outlet of said housing, said outer housing providing a second air channel between said housing and said outer housing, wherein said housing further comprises a first vent between said housing and said outer housing.

13. The mechanism of claim 12, wherein said first vent is positioned to be partially covered by a piston sidewall following actuation, wherein said first vent is dimensioned to provide for a substantially constant air velocity.

14. The mechanism of claim 12, further comprising:
an air reservoir; wherein said housing further comprises a second vent, said second vent communicating with said air reservoir.

15. The mechanism of claim 14, wherein said housing further comprises a bypass port having a first end which is closed by said piston sidewall when at rest, and a second end downstream from said piston,
and wherein said piston sidewall further comprises a bypass channel, which connects said bypass port and said air reservoir when said piston has moved toward housing distal end.

16. An aerosol delivery device comprising:

a) a device for holding a container, said container comprising:
   (i) at least one wall which is collapsible by the application of a force and having at least one opening, wherein said opening leads to an open channel having an end;
   (ii) a nozzle positioned at the end of the open channel;
   (iii) formulation in an amount of 100 milliliters or less in the container;

(b) a dispensing mechanism for forcing the formulation through the nozzle; and (c) a trigger mechanism according to claim 1.

17. A method of delivering an aerosolized formulation to the respiratory tract of an individual, comprising:
inhaling into the individual's respiratory tract a volume of a formulation using a device according to claim 16, wherein the dispensing mechanism is actuated when an inspiratory flow velocity generated by the individual exceeds a predetermined value within a range of 0.1 to 2.0 liters per second, thereby releasing a volume of formulation into the respiratory tract of the individual.

* * * * *